US006656898B1

(12) United States Patent
Foley et al.

(10) Patent No.: US 6,656,898 B1
(45) Date of Patent: Dec. 2, 2003

(54) ENZYME COMPOSITE PARTICLES HAVING AN ACIDIC BARRIER AND A PHYSICAL BARRIER COATING

(75) Inventors: Peter Robert Foley, Cincinnati, OH (US); Jeffrey Donald Painter, Loveland, OH (US); Mary Ruth Leyendecker, Cincinnati, OH (US); Eugene Steven Sadlowski, Cincinnati, OH (US); Brian Xiaoqing Song, West Chester, OH (US); Joseph Herbert Thien, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/937,353

(22) PCT Filed: Apr. 18, 2000

(86) PCT No.: PCT/US00/10389

§ 371 (c)(1), (2), (4) Date: Sep. 24, 2001

(87) PCT Pub. No.: WO00/63336

PCT Pub. Date: Oct. 26, 2000

Related U.S. Application Data

(60) Provisional application No. 60/130,045, filed on Apr. 19, 1999.

(51) Int. Cl.[7] .............................. C12S 9/00; C02F 5/02; C02F 5/08; C12N 9/96; B05D 7/00

(52) U.S. Cl. .................. 510/393; 510/392; 252/174.12; 435/188; 427/213

(58) Field of Search ................................ 510/392, 393; 252/174.12

(56) References Cited

U.S. PATENT DOCUMENTS

| | | | | | |
|---|---|---|---|---|---|
| 4,009,076 | A | * | 2/1977 | Green et al. | 427/154 |
| 4,965,012 | A | * | 10/1990 | Olson | 252/186.25 |
| 5,258,132 | A | * | 11/1993 | Kamel et al. | 428/402.24 |
| 5,733,763 | A | * | 3/1998 | Markussen et al. | 435/175 |

* cited by examiner

*Primary Examiner*—Yogendra N. Gupta
*Assistant Examiner*—Preeti Kumar
(74) *Attorney, Agent, or Firm*—Kevin L. Waugh

(57) ABSTRACT

A detersive enzyme composite particle suitable for incorporation in a liquid detergent composition is disclosed. The enzyme composite particle includes an enzyme containing core material, an acidic barrier layer coated on the enzyme containing core material, and a physical barrier layer coated on the acidic barrier layer.

15 Claims, 1 Drawing Sheet

ENZYME COMPOSITE PARTICLES HAVING AN ACIDIC BARRIER AND A PHYSICAL BARRIER COATING

This Application claims the benefit of Provisional Application Ser. No. 60/130,045 Filed Apr. 19, 1999.

TECHNICAL FIELD

The present invention relates to detersive enzyme composite particles having a an acidic barrier layer and a physical barrier layer. More particularly, the present invention relates to an enzyme particle, such as a prill, having an enzyme containing core which is coated with an acidic barrier layer and a physical barrier coating on the acidic barrier layer for the protection of the enzyme.

BACKGROUND OF THE INVENTION

The incorporation of detersive enzymes into dishwashing detergents is well known in the arena of both automatic dishwashing (ADW) formulas, and liquid hand dishwashing formulas (LDLs). A recognized need in ADWs compositions is to have present one or more ingredients which improve the removal of tough foods and stains (e.g., tea, coffee, cocoa, etc.) from consumer articles. Strong alkalis like sodium hydroxide, bleaches such as hypochlorite, builders such as phosphates and the like can help in varying degrees. Moreover, improved ADWs make use of a source of hydrogen peroxide, optionally with a bleach activator such as TAED, as noted. In addition, enzymes such as commercial proteolytic and amylolytic enzymes can be used. The alpha-amylase component provides at least some benefit with respect to the starchy soil removal properties of the ADW. ADWs containing amylases typically can also deliver a somewhat more moderate wash pH in use, and can remove starchy soils while avoiding delivering large weight equivalents of sodium hydroxide on a per-gram-of-product basis.

Typically, the enzyme component of a liquid ADW composition is added to the ADW composition in liquid form. While this allows the liquid ADW composition to have the benefits of enzyme content discussed above, there are also disadvantages, most notably that the liquid ADW composition must be formulated at pH levels that are lower than those conventionally used, because enzymes are rendered ineffectual after being exposed to high pH environments. Because formulating at lower pH levels can harm cleaning performance (high pH enhances cleaning by aiding the rates of hydration and hydrolysis), a need exists for an enzyme material that is stable in a high pH environment.

One approach to improving enzyme stability in a high pH (greater than 9) ADW detergent composition is to add the enzyme as a solid particle. This "enzyme particle" consists of a solid core enzyme material coated with a barrier layer material. For example, a solid enzyme material can be coated with a thick wax layer material to form an enzyme particle and then this enzyme particle may be added to the ADW composition.

But the use of these wax coatings have several disadvantages. Most notably, when the waxes melt and are released into the wash solution, due to the high temperature encountered during the automatic dishwashing process, they tend to cause undesirable filming on glass, stainless steel and plastic surfaces. This filming is a particular problem with ADW formulas, which often contain no significant surfactants in the composition. Additionally, thick wax coatings can also reduce the rate of dissolution of the enzyme-containing particle, which may reduce the cleaning contribution of the enzyme, by reducing the time it is resident in the wash solution.

Given the foregoing there is a continuing need to develop new compositions for the enzyme particles that will protect the enzyme core material when the particle is added to a high pH liquid ADW composition, and yet at the same time, not produce the undesirable filming associated with wax coatings, nor inhibit the rapid dissolution of the enzyme-containing particles.

Accordingly, it is a benefit of the present invention that an enzyme particle with a two-layer coating effectively protects the core enzyme material from high pH liquid compositions, without the deleterious effects of the thick wax layer coating noted above. This two-layer consists of an interior chemical barrier, preferably an acidic barrier, which is itself coated with an exterior physical barrier. The physical barrier prevents the chemical barrier from reacting directly with the alkaline liquid product (particularly important when the chemical barrier is an acidic barrier), while the chemical barrier effectively neutralizes any stray hydroxyl groups of the alkaline product that permeate past the physical barrier coating. The chemical and physical barrier thus work together and provide complementary functions. Preferred physical barriers include polymeric coatings that are insoluble in the liquid automatic dishwashing detergent composition but soluble, meltable or dispersable under the pH, temperature and agitation conditions of an ADW device.

In addition to their use in ADW compositions, these improved enzyme particles may be incorporated into light-duty liquid (LDL) detergent compositions useful for manual dishwashing as well. Enzymes, typically commercial proteolytic and amylolytic enzymes, provide LDL compositions with a variety of benefits, including improved cleaning performance as well as preferred skin mildness and "skin feel" aesthetics (i.e. the product does not feel slimy or slippery in the hands of a consumer). By adding enzymes to a LDL composition in the form of an enzyme particle, stability of enzymes in a LDL composition can be enhanced. Release of the enzymes is accomplished easily as a result of the agitation and increased temperature during manual dishwashing by the consumer.

BACKGROUND ART

U.S. Pat. No. 4,965,012 discloses an encapsulating enzyme composition.

U.S. Pat. Nos. 4,381,247; 4,707,287; 4,965,012; 4,973,417; 5,093,021 and 5,254,287 all disclose enzyme particles for granular detergent compositions. U.S. Pat. Nos. 4,526,698; 5,078,895; 5,332,518; 5,340,496; 5,366,655; 5,462,804 and WO/95/02670 all disclose coated bleach particles.

U.S. Pat. No. 5,200,236 discloses a method for wax encapsulating particles.

U.S. Pat. No. 3,908,045 discloses coating a solid bleach particle with a first layer of fatty acid and a second layer of base (alkali hydroxide) treated fatty acid.

SUMMARY OF THE INVENTION

The invention meets the needs above by providing a detersive enzyme composite particle suitable for incorporation in a liquid detergent composition, including, an enzyme containing core material, an acidic barrier layer coated on the enzyme containing core material, and a physical barrier layer coated on the acidic barrier layer.

DETAILED DESCRIPTION OF THE INVENTION

Figure 1:
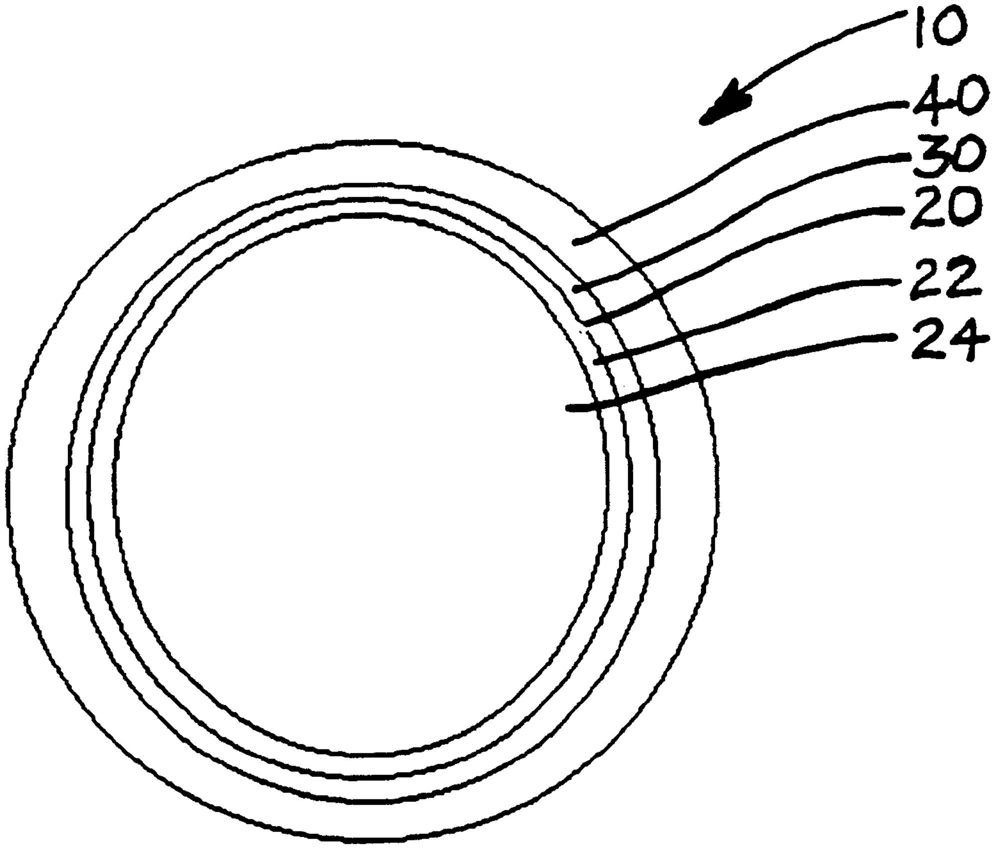
FIG. 1 is a cross-sectional view of the preferred embodiment of a composite enzyme particle of the present invention.

The present invention relates to composite enzyme particles for incorporation into detergent compositions, and in particular, into liquid automatic dishwashing compositions.

Referring now to FIG. 1, there is seen the composite particle 10 of the present invention. The particle 10 comprises an enzyme-containing core material 20 having an acidic barrier layer 30 coated thereon, and a physical barrier layer 40 coated on the acidic barrier layer 30. The enzyme core material itself comprises an enzyme layer 22 coated on carrier layer 24. The composite particle of the present invention, through the use of the acidic barrier layer, and the physical barrier layer, provides superior protection to the enzyme from degradation due to the alkalinity and other ingredients of a base liquid detergent as well as discoloration and odor generation. Accordingly, the enzyme particle of the present invention provides a significant advancement over the enzyme particles as known in the prior art.

Enzyme Containing Core Material

The enzyme containing core material, as the name implies, includes the enzyme or enzymes which the composite particle of the present invention is to deliver. The enzyme to be delivered by the present invention is a detersive enzyme. "Detersive enzyme", as used herein, means any enzyme having a cleaning, stain removing or otherwise beneficial effect in an automatic dishwashing composition. Preferred detersive enzymes are hydrolases such as proteases, amylases and lipases.

Enzymes are normally incorporated into detergent or detergent additive compositions at levels sufficient to provide a "cleaning-effective amount". The term "cleaning effective amount" refers to any amount capable of producing a cleaning, stain removal, soil removal, whitening, deodorizing, or freshness improving effect on substrates such as dishware and the like. In practical terms for current commercial preparations, typical amounts are up to about 5 mg by weight, more typically 0.01 mg to 3 mg, of active enzyme per gram of the detergent composition. Stated otherwise, the compositions herein will typically comprise from about 0.001% to about 15%, preferably about 0.01% to about 10% by weight of a commercial enzyme preparation. Protease enzymes are usually present in such commercial preparations at levels sufficient to provide from 0.005 to 0.1 Anson units (AU) of activity per gram of composition. For certain detergents, such as in automatic dishwashing, it may be desirable to increase the active enzyme content of the commercial preparation in order to minimize the total amount of non-catalytically active materials and thereby improve spotting/filming or other end-results. Higher active levels may also be desirable in highly concentrated detergent formulations. Accordingly, the enzyme particle of the present invention is formulated to deliver the desired amount of enzyme to the wash environment.

Suitable examples of proteases within the scope of the present invention are the subtilisins which are obtained from particular strains of *B. subtilis* and *B. licheniformis*. One suitable protease is obtained from a strain of Bacillus, having maximum activity throughout the pH range of 8–12, developed and sold as ESPERASE® by Novo Industries A/S of Denmark. hereinafter "Novo". The preparation of this enzyme and analogous enzymes is described in GB 1,243, 784 to Novo. Other suitable proteases include ALCALASE® from Novo and MAXATASE® from International Bio-Synthetics, Inc., The Netherlands; as well as Protease A as disclosed in EP 130,756 A, Jan. 9, 1985 and Protease B as disclosed in EP 303,761 A, Apr. 28, 1987 and EP 130,756 A, Jan. 9, 1985. See also a high pH protease from Bacillus sp. NCIMB 40338 described in WO 9318140 A to Novo. Enzymatic detergents comprising protease, one or more other enzymes, and a reversible protease inhibitor are described in WO 9203529 A to Novo. Other preferred proteases include those of WO 9510591 A to Procter & Gamble . When desired, a protease having decreased adsorption and increased hydrolysis is available as described in WO 9507791 to Procter & Gamble. A recombinant trypsin-like protease for detergents suitable herein is described in WO 9425583 to Novo.

In more detail, an especially preferred protease, referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76, preferably also in combination with one or more amino acid residue positions equivalent to those selected from the group consisting of +99, +101, +103, +104, +107, +123, +27, +105, +109, +126, +195, +197, +204, +206, +216, +260, +265, and/or +274 according to the numbering of *Bacillus amyloliquefaciens* subtilisin, with substitution, deletion or insertion of an amino acid residue in the following combination of residues: 76/99; 76/104; 76/99/104; 76/103/104; 76/104/107; 76/101/103/104; 76/99/101/103/104 and 76/101/10.4 of *B. amyloliquefaciens* subtilisin being preferred and 76/103/104 being the most preferred. Such enzymes are fully described in U.S. patent application Ser. Nos. 08/322,676 and 08/322,677, and in WO 95/10615 published Apr. 20, 1995 by Genencor International, the disclosures of which are herein incorporated by reference. Useful proteases are also described in PCT publications: WO 95/30010 published Nov. 9, 1995 by The Procter & Gamble Company; WO 95/30011 published Nov. 9, 1995 by The Procter & Gamble Company; WO 95/29979 published Nov. 9, 1995 by The Procter & Gamble Company.

Amylases suitable herein, especially for, but not limited to automatic dishwashing purposes, include, for example, α-amylases described in GB 1,296,839 to Novo: RAPIDASE®, International Bio-Synthetics, Inc. and TERMAMYL®, Novo. FUNGAMYL® from Novo is especially useful. Engineering of enzymes for improved stability, e.g., oxidative stability, is known. See, for example J. Biological Chem., Vol. 260, No. 11. Jun. 1985, pp. 6518–6521. Certain preferred embodiments of the present compositions can make use of amylases having improved stability in detergents such as automatic dishwashing types, especially improved oxidative stability as measured against a reference-point of TERMAMYL® in commercial use in 1993. These preferred amylases herein share the characteristic of being "stability-enhanced" amylases, characterized, at a minimum, by a measurable improvement in one or more of oxidative stability, e.g., to hydrogen peroxide/tetraacetylethylenediamine in buffered solution at pH 9–10; thermal stability, e.g., at common wash temperatures such as about 60° C.; or alkaline stability, e.g., at a pH from about 8 to about 11, measured versus the above-identified reference-point amylase. Stability can be measured using any of the art-disclosed technical tests. See, for example, references disclosed in WO 9402597. Stability-enhanced amylases can be obtained from Novo or from Genencor International. One class of highly preferred amylases herein have the commonality of being derived using site-directed mutagenesis from one or more of the Bacillus amylases, especially the Bacillus α-amylases, regardless of whether one, two or multiple amylase strains are the immediate precursors. Oxidative stability-enhanced amylases vs. the above-identified reference amylase are preferred for use, especially in bleaching, more preferably oxygen bleaching, as distinct from chlorine bleaching, detergent compositions herein. Such preferred amylases include (a) an amylase according to the hereinbefore incorporated WO 9402597, Novo, Feb. 3, 1994, as further illustrated by a mutant in which substitution is made, using alanine or threonine, preferably threonine, of the methionine residue located in position 197 of the *B. licheniformis* alpha-amylase, known as TERMAMYL®, or the homologous position variation of a similar parent amylase, such as *B. amyloliquefaciens, B. subtilis*, or *B. stearothermophilus*; (b) stability-enhanced amylases as described by Genencor International in a paper entitled "Oxidatively Resistant alpha-Amylases" presented at the 207th American Chemical Society National Meeting, Mar. 13–17 1994, by C. Mitchinson. Therein it was noted that bleaches in automatic dishwashing detergents inactivate alpha-amylases but that improved oxidative stability amylases have been made by Genencor from *B. licheniformis* NCIB8061. Methionine (Met) was identified as the most likely residue to be modified. Met was substituted, one at a time, in positions 8, 15, 197, 256, 304, 366 and 438 leading to specific mutants, particularly important being M197L and M197T with the M197T variant being the most stable expressed variant. Stability was measured in CASCADE® and SUNLIGHT®; (c) particularly preferred amylases herein include amylase variants having additional modification in the immediate parent as described in WO 9510603 A and are available from the assignee, Novo, as DURAMYL®. Other particularly preferred oxidative stability enhanced amylase include those described in WO 9418314 to Genencor International and WO 9402597 to Novo. Any other oxidative stability-enhanced amylase can be used, for example as derived by site-directed mutagenesis from known chimeric, hybrid or simple mutant parent forms of available amylases. Other preferred enzyme modifications are accessible. See WO 9509909 A to Novo.

Other amylase enzymes include those described in WO 95/26397 and in co-pending application by Novo Nordisk PCT/DK96/00056. Specific amylase enzymes for use in the detergent compositions of the present invention include α-amylases characterized by having a specific activity at least 25% higher than the specific activity of Termamyl® at a temperature range of 25° C. to 55° C. and at a pH value in the range of 8 to 10, measured by the Phadebas® α-amylas activity assay. (Such Phadebas® α-amylase activity assay is described at pages 9–10, WO 95/26397.) Also included herein are α-amylases which are at least 80% homologous with the amino acid sequences shown in the SEQ ID listings in the references. These enzymes are preferably incorporated into laundry detergent compositions at a level from 0.00018% to 0.060% pure enzyme by weight of the total composition, more preferably from 0.00024% to 0.048% pure enzyme by weight of the total composition.

Suitable lipase enzymes for detergent usage include those produced by microorganisms of the Pseudomonas group, such as *Pseudomonas stuizeri* ATCC 19.154, as disclosed in GB 1,372,034. See also lipases in Japanese Pat. Application 53,20487, laid open Feb. 24, 1978. This lipase is available from Amano Pharmaceutical Co. Ltd., Nagoya, Japan, under the trade name Lipase P "Amano," or "Arnano-P." Other suitable commercial lipases include Amano-CES, lipases ex *Chromobacter viscosum*, e.g. *Chromobacter viscosum* var. *lipolvticum* NRRLB 3673 from Toyo Jozo Co., Tagata, Japan; *Chromobacter viscosum* lipases from U.S. Biochemical Corp., U.S.A. and Disoynth Co., The Netherlands, and lipases ex *Pseudomonas gladioli*. LIPOLASE® enzyme derived from *Humicola lanuginosa* and commercially available from Novo, see also EP 341,947, is a preferred lipase for use herein. Lipase and amylase variants stabilized against peroxide enzymes are described in WO 9414951 A to Novo. See also WO 9205249 and DR 94359044.

In spite of the large number of publications on lipase enzymes, only the lipase derived from *Humicola lanuginosa* and produced in *Aspergillus oryzae* as host has so far found widespread application as additive for fabric washing products. It is available from Novo Nordisk under the tradename Lipolase™, as noted above. In order to optimize the stain removal performance of Lipolase, Novo Nordisk have made a number of variants. As described in WO 92/05249, the D96L variant of the native *Humicola lanuginosa* lipase improves the lard stain removal efficiency by a factor 4.4 over the wild-type lipase (enzymes compared in an amount ranging from 0.075 to 2.5 mg protein per liter). Research Disclosure No. 35944 published on Mar. 10, 1994, by Novo Nordisk discloses that the lipase variant (D96L) may be added in an amount corresponding to 0.001–100-mg (5–500,000 LU/liter) lipase variant per liter of wash liquor. The present invention provides the benefit of improved whiteness maintenance on fabrics using low levels of D96L variant in detergent compositions containing the mid-chain branched surfactant surfactants in the manner disclosed herein, especially when the D96L is used at levels in the range of about 50 LU to about 8500 LU per liter of wash solution.

Cutinase enzymes suitable for use herein are described in WO 8809367 A to Genencor.

A range of enzyme materials and means for their incorporation into synthetic detergent compositions is also disclosed in WO 9307263 A and WO 9307260 A to Genencor International, WO 8908694 A to Novo, and U.S. Pat. No. 3,553,139, Jan. 5, 1971 to McCarty et al. Enzymes are further disclosed in U.S. Pat. No. 4,101,457, Place et al, Jul. 18, 1978, and in U.S. Pat. No. 4,507,219, Hughes, Mar. 26, 1985. Enzyme materials useful for liquid detergent formulations, and their incorporation into such formulations, are disclosed in U.S. Pat. No. 4,261,868, Hora et al, Apr. 14, 1981. Enzymes for use in detergents can be stabilized by various techniques. Enzyme stabilization techniques are disclosed and exemplified in U.S. Pat. No. 3,600,319, Aug. 17, 1971, Gedge et al, EP 199,405 and EP 200,586, Oct. 29, 1986, Venegas. Enzyme stabilization systems are also described, for example, in U.S. Pat. No. 3,519,570. A useful Bacillus, sp. AC13 giving proteases, xylanases and cellulases, is described in WO 9401532 A to Novo.

In addition, mixtures of the above described enzymes may also be employed. In such instances, it is desirable to employ mixtures of protease enzymes. Particularly preferred are mixtures of chymotrypsin-like protease enzymes and trypsin-like protease enzymes.

The chymotrysin-like enzyrnes, according to the present invention, are those which have an activity ratio, as defined below, of greater than about 15. Particularly, preferred for this class of enzyme are those identified as "Protease D" above. Other chymotrypsin-like protease enzymes suitable for use in the present invention include those obtained from a strain of Bacillus, having maximum activity throughout the pH range of 8–12, developed and sold as ESPERASE® by Novo Industries A/S of Denmark, hereinafter "Novo". The preparation of this enzyme and analogous enzymes is described in GB 1,243,784 to Novo. Other suitable proteases include ALCALASE® from Novo as well as the proteases known as BPN' and Carlsberg.

The trypsin-like enzymes, according to the present invention, are those which have an activity ratio, as defined below, of less than about 10, preferably less than about 8. Particularly suitable protease enzymes meeting the above requirement are microbial alcaline proteinases such as the protease enzyme obtained from *Bacillus Lentus* subtilisin including those commercially available under the tradenames SAVINASE® from Novo and PURAFECT® from Genencor International.

Other particularly preferred trypsin-like protease enzymes according to the present invention include those which are non-naturally-occurring carbonyl hydrolase variants which are derived by replacement of a plurality of amino acid residues of a precursor carbonyl hydrolase corresponding to position +210 in combination with one or more of the following residues: +33, +62, +67, +76, +100, +101, +103, +104, +107, +128, +129, +130, +132, +135, +156, +158, +164, +166, +167, +170, +209, +215, +217, +218, and +222, where the numbered position corresponds to naturally-occurring subtilisin from *Bacillus amyloliquefaciens* or to equivalent amino acid residues in other carbonyl hydrolases or subtilisins, such as *Bacillus lentus* subtilisin with different amino acids.

The preferred variant protease enzymes useful for the present invention comprise the substitution, deletion or insertion of amino acid residues in the following combinations: 210/156; 210/166; 210/76; 210/103; 210/104; 210/217; 210/156/166; 210/156/217; 210/166/217; 210/76/156; 210/76/166; 210/76/217; 210/76/156/166; 210/76/156/217; 210/76/166/217; 210/76/103/156; 210/76/103/166; 210/76/103/217; 210/76/104/156; 210/76/104/166; 210/76/104/217; 210/76/103/104/156; 210/76/103/104/166; 210/76/103/104/217; 210/76/103/104/156/166; 210/76/103/104/156/217; 210/76/103/104/166/217 and/or 210/76/103/104/156/166/217; 210/76/103/104/166/222; 210/67/76/103/104/166/222; 210/67/76/103/104/166/218/222. Most preferably the variant enzymes useful for the present invention comprise the substitution, deletion or insertion of an amino acid residue in the following combination of residues: 210/156; 210/166; 210/217; 210/156/166; 210/156/217; 210/166/217; 210/76/156/166; 210/76/103/156/166 and 210/76/103/104/156/166 of *B. lentus* subtilisin with 210/76/103/104/156/166 being the most preferred.

The protease enzymes useful herein encompass the substitution of any of the nineteen naturally occurring L-amino acids at the designated amino acid residue positions. Such substitutions can be made in any precursor subtilisin (procaryotic, eucaryotic, mammalian, etc.). Throughout this application reference is made to various amino acids by way of common one and three-letter codes. Such codes are identified in Dale, M. W. (1989), *Molecular Genetics of Bacteria*, John Wiley & Sons, Ltd., Appendix B.

Preferably, the substitution to be made at each of the identified amino acid residue positions include but are not limited to substitutions at position +210 including I, V, L, and A, substitutions at positions +33, +62, +76, +100, +101, +103, +104, +107, +128, +129, +130, +132, +135, +156, +158, +164, +166, +167, +170, +209, +215, +217, and +218 of D or E, substitutions at position 76 including D, H, E, G, F, K, P and N: substitutions at position 103 including Q, T, D, E, Y, K, G, R and S; and substitutions at position 104 including S, Y, I, L, M, A, W,.D, T, G and V; and substitutions at position 222 including S, C, A.

Specificty/Activity Ratio

Substrate specificity is generally illustrated by the action of an enzyme on two synthetic substrates. An enzyme is placed in a solution with one of the two synthetic substrates. The capability of the enzyme in question to hydrolyze the synthetic substrate is then measured. For the purposes of the present invention, the synthetic substrates employed to measure the specificity of the enzymes of the present invention are the synthetic substrate N-Succinyl-alanyl-alanyl-prolyl-phenylalanyl-p-Nitroanilide, hereinafter suc-AAPF-pNA, and the synthetic substrate N-Benzyl-valyl-araganyl-lysyl-p-Nitroanilide, hereinafter bVGA-pNA, both of which are available from SIGMA Chemicals. Both of these synthetic substrates are well-known to one of ordinary skill in the art. A protease in the class of enzymes having trypsin-like specificity preferentially hydrolyze the synthetic substrate bVGR-pNA but hydrolyze the synthetic substrate sucAAPF-pNA to a much lesser extent. Conversely, chymotrypsin-like protease enzymes preferentially hydrolyze the synthetic substrate bVGR-pNA but hydrolyze suc-AAPF-pNA to a much-lesser extent.

The overall specificity of a protease enzyme can then be determined by measuring that enzyme's specificty against each of the synthetic substrates and then taking a ratio of that enzyme's activity on the two synthetic substrates. Accordingly, for the purposes of the present invention, the activity specificty ratio is determined by the formula:

[activity on suc-AAPF-pNA]/[activity on bVGR-pNA]

An enzyme having a ratio of less than about 10, more preferably less than about 8 and most preferably less than about 7 may then be considered to demonstrate trypsin-like specificty for the purposes of the present invention while an enzyme having a ratio greater than about 15, preferably greater than about 17.5 and most preferably greater than about 20 may be considered to demonstrate chymotrypsin-like Specificty for the purposes of the present invention.

For the purposes of the present invention, specificity is measured and determined against the two synthetic substrates as detailed above. The following test was employed. 5 mls of a Trisma buffer at a pH of 8.6 (prepared from a combination of 12.109 g Tris Base (0.1M), 1.471 g $CaCl_2.2H_2O$ (0.01 M), 3.1622 g $Na_2S_2O_3$ (0.02 M) pH adjusted with 1N $H_2SO_4$) and a temperature of 25° C. is added to a standard 10 ml test tube. 0.5 ppm of the active enzyme to be tested in a 1M glycine buffer is added to the test tube. Approximately, 1.25 mg of the synthetic substrate per mL of buffer solution is added to the test tube. The mixture is allowed to incubate for 15 minutes at 25° C. Upon completion of the incubation period, an enzyme inhibitor, PMSF. is added to the mixture at a level of 0.5 mg per mL of buffer solution. The absorbency or OD value of the mixture is determined on a Gilford Response UV spectrometer, Model # 1019 read at a visible light 410 nm wavelength. The absorbence then indicates the activity of the enzyme on the synthetic substrate. The greater the absorbence, the higher the level of activity against that substrate. Accordingly, absorbence is equal to enzyme activity for purposes of the present invention.

The mixed protease enzyme system of the present invention is employed in compositions at higher-end levels of from less than about 10%, more preferably less than about 5% and even more preferably less than about 2% and at lower-end levels of from greater than about 0.0001%, more preferably greater than about 0.1% and even more preferably greater than about 0.5% by weight of the composition. As for within the system itself, the ratio of chymotrypsin-like protease enzyme to trypsin-like protease enzyme ranges from about 0.5: 1 to about 10:1 and more preferably from about 2:1 to about 5:1 and most preferably from about 1:1 to about 3:1. Also, preferably the protease enzyme is present in the compositions in an amount sufficient to provide a ratio of mg of active protease per 100 grams of composition to ppm theoretical Available $O_2$ ("$AvO_2$") from any peroxyacid in the wash liquor, referred to herein as the Enzyme to Bleach ratio (E/B ratio), ranging from about 1:1 to about 20:1. Several examples of various cleaning compositions wherein the protease enzymes may be employed are discussed in further detail below.

Core Manufacture

The manufacture of the core material herein comprising the enzyme can be conducted using a variety of methods, according to the desires of the formulator and the available equipment. The following illustrate various methods of manufacture, and are included for the convenience of the formulator and not by way of limitation.

The particles herein can be formulated as "marumes". Marumes and their manufacture are disclosed in U.S. Pat. No. 4,016,041 and British 1,361,387. Marumes can be prepared using an apparatus known under the trademark "Marumerizer" from Fuji Paudal, KK, and is described in U.S. Pat. No. 3,277,520 and German 1,294,351. Basically, the formation of marumes involves spheronizing extrudate noodles comprising the enzyme and a carrier. The extrudate is fed into the Marumizer™ apparatus, which operates by centrifugal force on the noodles to form them into spheronized particles, referred to as "marumes".

In yet another method, the core layer herein can be manufactured in the form of "prills". Basically, in this method a slurry comprising the enzyme and a carrier melt is introduced through a spray head into a cooling chamber. The particle size of the resulting prills can be controlled by regulating the size of the spray drops of the slurry. The size of the drops will depend on the viscosity of the slurry, the spray pressure, and the like. The manufacture of prills is more fully disclosed in U.S. Pat. No. 3,749,671.

In still another method, the particles herein are made by a process comprising the following basic steps:

(i) combining the particles the dried enzyme with a carrier material while the carrier material is in a softened or molten state while agitating this combination to form a substantially uniform admixture;

(ii) rapidly cooling the resultant admixture in order to solidify it; and thereafter (iii) further working the resulting solidified admixture, as necessary, to form the desired composite particles.

In yet another method, commercially available core materials may also be employed which may then be coated with an enzyme layer as described in U.S. Pat. No. 4,707,287, the disclosure of which is herein incorporated by reference.

Preferred methods for manufacturing the particles herein include: building-up of layers of carrier in a fluidized bed, Wurster-type coater, drum granulation, pan coaters, and like techniques for building up a granule by adding consecutive layers on top of a core material, all of which are well-known to those skilled in the art of particle manufacture. A typical process suitable for use in the manufacture of the composite particles herein is described in detail in U.S. Pat. No. 5,324,649, incorporated herein by reference.

Acidic Barrier Layer

In the preferred embodiment, the acidic barrier layer is formed from materials selected from the group consisting of organic acids, inorganic acids or polyeric-acids. When the acidic barrier layer is formed from organic acids, the organic acids are selected from the group consisting of citric acid, maleic acid, malic acid, glutamic acid, succinic acid, and mixtures thereof. When the acidic barrier layer is formed from inorganic acids, the inorganic acids arc selected from the group consisting of hydrochloric acid, sulfuric acid, nitric acid, and mixtures thereof and further, the inorganic acids absorbed in or adsorbed on polymeric coatinos formed from materials selected from the group consisting of alkyl cellulose, polyvinyl alcohol, polyethylene glycol, alginate, polyvinylidene chloride, fluorocarbons and mixtures thereof. When the acidic barrier layer is formed from polymeric acids, the polymeric acids are selected from the group consisting of non-neutralized or partially neutralized polyacrylic acid, modified polyacrylic acid, and mixtures thereof.

In the preferred embodiment, the acidic barrier layer is non-hygroscopic. The non-hygroscopicity is defined as thus: the acidic barrier layer is non-hygroscopic such that the acidic barrier layer absorbs no greater than about 20% moisture by weight of the acidic barrier layer, the acidic barrier is exposed to 80% relative humidity for a period of about 1 week.

Physical Barrier Coating

In the preferred embodiment, the enzyme particles have a combination of an acidic barrier coating and a physical barrier coating for enhanced protection of the enzyme particle. The enzyme particle is first coated with a chemical barrier coating and then with a physical barrier coating. This provides a two-fold protection to the enzyme particle. The physical barrier coating effectively protects the enzyme particle from the bulk alkalinity of the liquid ADW compositions. The chemical barrier effectively neutralizes any stray hydroxyls that permeate past the physical barrier coating, which can be formed from polymers and waxes.

In one aspect of the present invention, physical barrier coating is formed from a polymeric coating. The polymeric coating is prepared from materials selected from the group consisting of alkyl cellulose ethers and polyvinyl alcohol. Other materials include paraffin waxes, bees wax, wax esters, paraffin wax and petrolatum mixture in a ratio in a range of from 30:1 to about 10:1 by weight, paraffin wax and silicon mixture, paraffin wax, mica and silicon mixtures, and paraffin wax, mica and petrolatum mixture. Alternative materials for the physical barer include flurocarbons and polyvinylidene chloride. Alternatively, the coating is prepared from alginate. The particles remain undissolved in the liquid automatic dishwashing detergent composition until the composition is used in an automatic dishwasher. The liquid automatic dishwashing detergent product does not cause an increase in filming of glassware or dishware as compared to a liquid automatic dishwashing detergent product not having the above particles.

In the preferred embodiment, the acid barrier coated enzyme particles are further coated with a polymeric coating which is insoluble in the liquid automatic dishwashing detergent composition but soluble in automatic dishwashing wash solution. The polymeric coating is prepared from materials selected from the group consisting of alkyl cellulose ethers. Desirably, the alkyl cellulose ethers are methyl cellulose and hvdroxypropyl methyl cellulose (HPMC). Preferably, the polymeric coating is prepared from methyl cellulose having a number average molecular weight desirably in a range of from about 5000 to about 100,000, more preferably from about 10,000 to about 20,000, and most preferably, about 14,000. The preferred methyl cellulose is one sold under the trade name Methocel A15LV, and manufactured by Dow Chemicals. Alternatively, the polymeric coating is polyvinyl alcohol (PVA) having a molecular weight, desirably in a range of from about 5000 to about 100,000, and preferably from about 13,000 to about 23,000. The preferred PVA is from about 87% to about 89% hydrolyzed, such as a commercially available product having a trade name Airvol 205.

Process for Forming Polymeric Coating on Particles Coated with Acidic Barrier The process by which the polymeric coating is prepared and deposited upon the acid barrier coated enzyme particle is critical in order for the enzyme particles to remain undissolved in the liquid automatic dishwashing detergent composition and only become soluble in the wash solution during automatic dishwashing. It is desirable that the particles dispersed in the liquid ADW compositions do not break up or dissolve in the composition. It is also desirable that this be achieved without depositing an unduly thick coating of a polymeric material on the particle. It has been surprisingly discovered that when the polymeric material, such as methyl cellulose is sufficiently hydrated before spraying on the particle or prill, the polymer coated particle or prill remains stable, unbroken and undissolved in the liquid ADW composition. This hydration is achieved by forming a sprayable aqueous solution of the polymer (alkyl cellulose ether and/or polyvinyl alcohol) having a polymer concentration desirably in a range of from about 1% to about 30% by weight, preferably in a range of about 3% to about 20%, more preferably in a range of about 3% to about 10%, and most preferably, about 5%. Further, the temperature of aqueous solution of the polymer is desirably maintained within a range of from about 30° C. to about 40° C. while spraying the polymer solution on the particle, and preferably in a range of from about 32° C. to about 38° C., and most preferably at a temperature of about 35° C. It has been surprisingly found that by using a combination of the above process steps, i.e., the polymer solution being in a range of from about 1% to 30% by weight, and the spray temperature being in a range of from about 30° C. to about 40° C., that a very stable, unbroken, continuous coating is formed on the particle or prill which is undissolved in the liquid ADW composition but soluble in the wash solution, while at the same time, requiring only about 5% polymer by weight of the particle. This offers an advantage because by using a smaller the quantity of polymer used for coating the enzyme particle, there is a reduction in the amount of polymer residue that can potentially redeposit on the dishware and dishwasher, when the particle dissolves in the wash solution.

The enzyme particles may optionally be colored, or whitened, using dyes or pigments. In one embodiment, the enzyme particles are colored and an automatic dishwashing liquid detergent composition is clear or translucent, so as to make the liquid automatic dishwashing product aesthetically pleasing. In another embodiment, the enzyme particles and the liquid dishwashing detergent composition are both colored and the color of the particles is matched to the base color of the liquid composition. In one embodiment, the enzyme particles have a dark green color whereas the liquid composition has a light green color. Other preferred color combinations for the polymeric coating on the enzyme particles and the liquid automatic dishwashing composition are: blue:blue, blue:white, green:green, green:white and green:yellow, respectively.

Desirably, the enzyme particles comprise from about 0.1% to about 5.0% by weight of the liquid composition, and preferably, from about 0.2% to about 1.0% by weight of the liquid composition.

The enzyme particles can be formed from various materials that do not cause any detrimental affect upon the performance of the liquid contains an enzyme, such as a prill. The core is coated with an acidic barrier coating and a polymeric coating as described before. The core can be made from sucrose, as an example. The method of forming prills is well known to those skilled in the art and is disclosed in the literature, such as for example, in U.S. Pat. No. 4,965,012, which is incorporated herein by reference.

The enzyme particles can be of various sizes and shapes, such as spherical, oval, cylindrical or polygonal and desirably have a particle size in a range of from about 200 μm to about 5000 μm, preferably, from about 400 μm to about 2000 μm, and most preferably, from about 500 μm to about 850 μm.

Carrier Material

The composite particles herein may be manufactured using one or more "carrier" materials as described above which incorporate enzyme in a matrix. Since the enzyme is intended for use in an aqueous medium, the carrier material should dissolve or readily disperse in water under the intended use conditions in order to release the enzyme to perform its detersive functions. The carrier material should be inert to reaction with the enzyme components of the particle under processing conditions and after granulation. Additionally, the carrier material should preferably be substantially free of moisture present as unbound water, as noted hereinafter.

In one mode, the carrier for the soluble or dispersible composite enzyme particles herein can comprise a mixture of an inert, water-dispersible or water-soluble, typically inorganic granule material and a binder. The binder serves to provide integral particles containing the enzyme and granule material. Such particles will typically comprise: from about 50% to about 95%, by weight, of the granule material; from about 5% to about 50%, by weight, of the binder: and from about 0.01% to about 15%, by weight, of the enzyme.

Granule materials useful in such particles include inert, inorganic salts. By "inert" is meant that the salts do not deleteriously interact With the enzyme. Non-limiting examples include sodium sulfate, sodium carbonate, sodium silicate, and other ammonium and alkali metal sulfates, carbonates and silicates, and the like.

Examples of suitable organic binders include the water soluble organic homo- or co-polymeric polycarboxylic acids or their salts in which the polycarboxylic acid comprises at least two carboxyl radicals separated from each other by not more than two carbon atoms. Polymers of the latter type are disclosed in GB-A-1,596,756. Preferred examples of such compounds are the polymers which contain acrylic acid, that is to say homopolymers of acrylic acid and copolymers with any suitable other monomer units, and which have a average molecular weight of from 2,000 to 100,000. Suitable other monomer units include modified acrylic, fumaric, maleic, itaconic, aconitic, mesaconic, citraconic and methylenemalonic acid or their salts, maleic anhydride, acrylamide, alkylene, vinylmethyl ether, styrene and any mixtures thereof. Preferred are the copolymers of acrylic acid and maleic anhydride having a average molecular weight of from 20,000 to 100,000.

Preferred acrylic acid containing polymers have an average molecular weight of less than 15,000, and include those sold under the tradename Sokalan PA30, PA20, PA15, PA10 and Sokalan CP10 by BASF GmbH, and those sold under the tradename Acusol 445N by Rohm and Haas. Other suitable polymers include Acusol 450N and 410N.

Other preferred acrylic acid containing copolymers include those which contain as monomer units: a) from 90% to 10%, preferably from 80% to 20% by weight acrylic acid or its salts and b) from 10% to 90%, preferably from 20% to 80% by weight of a substituted acrylic monomer or its salts having the general formula —[$CR_2$—$CR_1$(CO—O—$R_3$)]— wherein at least one of the substituents $R_1$, $R_2$ or $R_3$, preferably $R_1$ or $R_2$ is a 1 to 4 carbon alkyl or hydroxyalkyl group, $R_1$ or $R_2$ can be a hydrogen and $R_3$ can be a hydrogen or alkali metal salt. Most preferred is a substituted acrylic monomer wherein $R_1$ is methyl, $R_2$ is hydrogen (i.e. a methacrylic acid monomer). The most preferred copolymer of this type has a average molecular weight of from 4500 to 3000 and contains 60% to 80% by weight of acrylic acid and 40% to 20% by weight of methacrylic acid. A suitable example includes Acusol 480N available from Rohm & Haas.

The polyamino compounds are useful as organic binders herein including those derived from aspartic acid such as those disclosed in EP-A-305282, EP-A-305283 and EP-A-351629.

Terpolymers containing monomer units selected from maleic acid, acrylic acid, pojyaspartic acid and vinyl alcohol, particularly those having an average molecular weight of from 5,000 to 10,000, are also suitable herein.

Other organic binders suitable herein include essentially any charged and non charged cellulose derivatives such as methylcellulose, carboxymethylcellulose, hydroxypropylmethylcellulose, hydroxyethylcellulose, and ethylhydroxyethylcellulose.

Other suitable binders include the $C_{10}$–$C_{20}$ alcohol ethoxylates containing from 5–100 moles of ethylene oxide per mole of alcohol and more preferably the $C_{15}$–$C_{20}$ primary alcohol ethoxylates containing from 20–100 moles of ethylene oxide per mole of alcohol.

Other preferred binders include polyvinyl alcohol, polyvinyl alcohol, the polyvinylpyrrolidones with an average molecular weight of from 12,000 to 700,000 and the polyethylene glycols (PEG) with an average molecular weight of from 600 to $5\times10^6$ preferably 1000 to 400,000 most preferably 1000 to 10,000. Copolymers of maleic anhydride with ethylene, methylvinyl ether or methacrylic acid, the maleic anhydride constituting at least 20 mole percent of the polymer are further examples of polymeric materials useful as binder agents. These polymeric materials may be used as such or in combination with solvents such as water, propylene glycol and the above mentioned $C_{10}$–$C_{20}$ alcohol ethoxylates containing from 5–100 moles of ethylene oxide per mole. Further examples of binders include the $C_{10}$–$C_{20}$ mono- and diglycerol ethers and also the $C_{10}$–$C_{20}$ fatty acids.

Other carrier materials suitable for use in the manufacture of the composite particles herein include, by way of illustration and not limitation: polyethylene glycols ("PEG") having a molecular weight typically in the range from about 1400 to about 35,000 (PEG 1400-PEG 35000) and preferably having a melting point in the range from about 38° C. to about 77° C.; fatty acids and/or fatty amides preferably having a melting point in the range from about 38° C. to about 77° C.; fatty alcohols preferably having a melting point in the range from about 38° C. to about 77° C.; the condensation products of ethylene oxide or mixed ethylene/propylene oxide and/or such condensation products of EO and/or PO with a linear or branched-chain alcohol and preferably having a melting point in the range from about 38° C. to about 77° C.; and mixtures of the foregoing. Paraffin waxes, preferably having a melting point in the range from about 38° C. to about 77° C., can also be used singly, or in combination with the foregoing carrier materials.

Also suitable as carrier materials are paraffin waxes which should melt in the range of from about 38° C. (100° F.) to about 43° C. (110° F.), $C_{16}$–$C_{20}$ fatty acids and ethoxyl $C_{16}$–$C_{20}$ alcohols. Mixtures of suitable carrier materials are also envisaged.

Various other materials may be used in the carrier, including finely divided cellulosic fibers (see U.S. Pat. No. 4,106,991) sugars, starches, and the like, according to the desires of the formulator. If used, such other materials will typically comprise from about 2% to about 50%. by weight, of the composite particles herein.

In the preferred embodiment, the composite enzyme particles have a spherical shape, and a diameter of about 5 mm, are formed from a sucrose core coated with an acidic barrier coating formed from citric acid, and further coated with a polymeric coating formed from methyl cellulose, and having a bluish-green color. The particles are incorporated into a liquid ADW composition to form a liquid ADW product, wherein the particles comprise about 0.1% to about 5% by weight of the liquid ADW product. The particles contain a mixture of protease and amylase enzymes. The particles are insoluble in the liquid. ADW composition but are soluble in the wash solution during automatic dishwashing.

Accordingly, having thus described the invention in detail, it will be obvious to those skilled in the art that various changes may be made without departing from the scope of the invention and the invention is not to be considered limited to what is described in the specification.

What is claimed is:

1. A detersive enzyme composite particle suitable for incorporation in a liquid detergent composition, comprising:

a) an enzyme containing core material;

b) an acidic barrier layer coated on said enzyme containing core material; wherein said acidic barrier layer is formed from one or more organic acids and inorganic acids, wherein said organic acids are selected from the group consisting of citric acid, maleic acid, malic acid, glutamic acid, and succinic acid and wherein said inorganic acids are selected from the group consisting of hydrochloric acid and nitric acid and c) a physical barrier layer coated on said acidic barrier layer.

2. The composite particle according to claim 1, wherein said acidic barrier layer is non-hygroscopic such that said acidic barrier layer absorbs no greater than about 20% moisture by weight of said acidic barrier layer, when said acidic barrier is exposed to 80% relative humidity for a period of about 1 week.

3. The composite particle according to claim 1, wherein said acidic barrier layer is formed from materials selected from the group consisting of organic acids, inorganic acids polymeric acids, and mixtures thereof, wherein said materials do not generate a gas during neutralization.

4. The composite particle according to claim 1, wherein said acidic barrier layer is formed from materials selected from inorganic acids, wherein said inorganic acids are absorbed in or adsorbed on polymeric coatings formed from materials selected from the group consisting of alkyl cellulose, polyvinyl alcohol, polyethylene glycol, alginate, polyvinylidene chloride and mixtures thereof.

5. The composite particle according to claim 1, wherein said physical barrier coating is insoluble in said liquid detergent composition but one or more of soluble, meltable or dispersible in a wash solution.

6. The composite particle according to claim 5, wherein said physical barrier coating is formed from polymeric materials selected from the group consisting of alkyl cellulose ethers and polyvinyl alcohol.

7. The composite particle according to claim 5, wherein said physical barrier coating is formed from methyl cellulose.

8. The composite particle according to claim 7, wherein said physical barrier coating is formed from methyl cellulose having a molecular weight in a range of from about 5,000 to about 100,000.

9. The composite particle according to claim 8, wherein said physical barrier coating is present in an amount in a range of about 1% to about 20% by weight of said composite particle.

10. The composite particle according to claim 1, wherein said physical barrier coating is formed from a wax.

11. The composite particle according to claim 10, wherein said waxes are selected from the group consisting of paraffin wax, bees wax, wax ester, paraffin wax and petrolatum mixture in a ratio in a range of from 30:1 to about 10:1 by weight, paraffin wax and silicon mixture, paraffin wax, mica and silicon mixture, paraffin wax, mica and petrolatum mixture.

12. The composite particle according to claim 10, wherein said waxes are selected from the group consisting of flurocarbons and polyvinylidene chloride.

13. The composite particle according to claim 1, wherein said physical barrier coating is formed from alginate.

14. The composite particle according to claim 1, wherein said enzyme containing core material comprises a protease enzyme.

15. The composite particle according to claim 1, wherein said enzyme core material comprises a mixture of at least two-different protease enzymes.

* * * * *